US006474334B1

(12) United States Patent
Lemer

(10) Patent No.: US 6,474,334 B1
(45) Date of Patent: Nov. 5, 2002

(54) MULTIPLEX VENTILATION SYSTEM

(75) Inventor: Joseph Lemer, Haifa (IL)

(73) Assignee: North Wind Ltd., Haifa (IL)

( * ) Notice: Subject to any disclaimer, the term of this patent is extended or adjusted under 35 U.S.C. 154(b) by 0 days.

(21) Appl. No.: 09/630,558

(22) Filed: Aug. 2, 2000

(30) Foreign Application Priority Data

Aug. 3, 1999 (IL) ................................................ 131232

(51) Int. Cl.⁷ ............................................ A61M 15/00
(52) U.S. Cl. ............................ 128/204.18; 128/204.21; 128/204.26
(58) Field of Search ................... 128/204.18, 204.21, 128/204.22, 204.23, 204.25, 204.26, 206.27, 205.26

(56) References Cited

U.S. PATENT DOCUMENTS

| | | | | |
|---|---|---|---|---|
| 2,934,293 A | * | 4/1960 | Boehme et al. | 128/206.27 |
| 4,495,946 A | * | 1/1985 | Lemer | 128/204.25 |
| 4,510,930 A | * | 4/1985 | Garcia | 128/205.24 |
| 5,918,596 A | * | 7/1999 | Heinonen | 128/204.21 |
| 6,187,099 B1 | * | 2/2001 | Blaudszun | 118/708 |

FOREIGN PATENT DOCUMENTS

| | | |
|---|---|---|
| GB | 2057273 | 2/1983 |
| IL | 58185 | 1/1982 |

OTHER PUBLICATIONS

Lemer, J. et al., "Fiberoptic Bronchoscopy with General Anesthesia Using a Transvector for Ventilation", Chest, vol. 90, No. 4, Oct. 1986, pp. 613–614.

Brauer (HMC–BRAUER Ltd.), "Airmovers", product description, England, 1987, pp. 1–8.
VORTEC Corp., "Blow Off", product description, USA, 1978, pp. 1–6.
VORTEC Corp., "Transvector Air Flow Amplifiers", pp. 1–4, 1979, USA.
VORTEC Corp., "A Short Course on Transvector™ Air Flow Amplifiers with Application Notes", pp. 1–8, 1976, USA.
VORTEC Corp., "A Short Course on Vortex Tubes and Application Notes", pp. 1–7, USA, 1974.

* cited by examiner

Primary Examiner—Aaron J. Lewis
Assistant Examiner—Michael Mendoza
(74) Attorney, Agent, or Firm—Pillsbury Winthrop LLP

(57) ABSTRACT

A ventilation system including a manifold fluidly connectable at an inlet thereof to a pressurized source of a driving gas, the manifold having a plurality of branches, an electronically controlled valve fluidly connected to each branch downstream of the inlet of the manifold, a ventilator fluidly connected to each of the branches downstream of the valves, each ventilator being operative to force a driving gas into lungs of a patient, and a controller in electrical communication with the valves, the controller operating the valves in accordance with an operating cycle including: a) causing a driving gas to flow through one of the ventilators while substantially preventing flow of the driving gas through the other ventilators, b) causing the driving gas to flow to another one of the ventilators which previously had no driving gas flowing therethrough, while substantially preventing flow of the driving gas through the other ventilators including the ventilator which previously had the driving gas flowing therethrough, and c) sequentially repeating steps a) and b) until all the ventilators have had the driving gas flow therethrough.

16 Claims, 6 Drawing Sheets

MULTIPLEX VENTILATION SYSTEM

FIELD OF THE INVENTION

The present invention relates generally to a device for causing artificial respiration through an endotracheal tube or breathing mask, and particularly to such a device which permits simultaneous ventilation of a multiplicity of patients.

BACKGROUND OF THE INVENTION

In certain medical procedures, it is necessary to perform direct artificial respiration by pumping air or oxygen into a patient's lungs, which is then exhaled by the natural elastic recoil of the walls of the chest cavity, diaphragm and the lungs.

A particularly advantageous artificial breathing device, herein also referred to as a ventilator, is disclosed in U.S. Pat. No. 4,495,946 to the present inventor, the disclosure of which is incorporated herein by reference. This device may be attached by an unobstructed air duct to an outer end of a flexible endotracheal tube or breathing mask. A regulating valve is provided with its inlet side connected to an oxygen supply or other compressed gas and its outlet side connected to the unobstructed air duct through a small-bore venturi tube which extends close and generally parallel to the air duct wall in a direction towards the endotracheal tube or breathing mask. Oxygen or other compressed gas passing through the venturi into the air duct at great velocity draws air from the outside environment by injector action and presses it into the lungs of a patient. Air is then expelled by the elasticity of the lungs and the chest cavity, and can freely escape through the unobstructed air duct, which likewise permits the ejection of mucus, blood and other excretions.

SUMMARY OF THE INVENTION

The present invention seeks to provide several improvements to the ventilator disclosed in U.S. Pat. No. 4,495,946.

One object of the present invention is to provide a multiplex ventilating system capable of ventilation of a multiplicity of patients. This system is particularly advantageous for ventilating patients in a mass emergency situation such as persons whose breathing has been impaired by substances of chemical/biological warfare, for example. The system includes a central control box which is essentially a pneumatically driven, electronically controlled flow divider. The driving gas, e.g., pressurized oxygen or air, is divided by branches and directed to a plurality of ports which are fluidly connected to tubing which directs the oxygen or air to the lungs of patients.

It is known that normally, physiologically, the ratio inhalation to exhalation in a human is in the range of about 1:2 to 1:3. The present invention exploits this fact and has an operating cycle wherein at each point of the cycle, oxygen or air is pressed into the lungs of one patient, while at the same time two, or most preferably three, other patients are in exhalation. In this manner, four patients, for example, can be simultaneously ventilated at the rate of 10–15 cycles per minute. This rate is considered quite satisfactory, since for a normal person, the rate is about 12 cycles per minute. The system preferably has symmetric branches such that 8 or more persons can be simultaneously ventilated.

A particular advantage of the present invention is that at any time only one quarter of the patients are actually drawing on the available pressure supply. This is in sharp contrast to prior art systems wherein all of the patients draw on the available pressure supply, possibly simultaneously, which is wasteful and expensive.

Another object of the present invention is to provide further improvements to U.S. Pat. No. 4,495,946, such as enhancing the driving gas (e.g., oxygen enrichment or additional moisturizing), endotracheal pressure measurement, flow measurement and ventilation by means of a transvector.

There is thus provided in accordance with a preferred embodiment of the present invention a ventilation system including a manifold fluidly connectable at an inlet thereof to a pressurized source of a driving gas, the manifold having a plurality of branches, an electronically controlled valve fluidly connected to each branch downstream of the inlet of the manifold, a ventilator fluidly connected to each of the branches downstream of the valves, each ventilator being operative to force a driving gas into lungs of a patient, and a controller in electrical communication with the valves, the controller operating the valves in accordance with an operating cycle including:

a) causing a driving gas to flow through one of the ventilators while substantially preventing flow of the driving gas through the other ventilators, b) causing the driving gas to flow to another one of the ventilators which previously had no driving gas flowing therethrough, while substantially preventing flow of the driving gas through the other ventilators including the ventilator which previously had the driving gas flowing therethrough, and c) sequentially repeating steps a) and b) until all the ventilators have had the driving gas flow therethrough.

In accordance with a preferred embodiment of the present invention each branch divides into two sub-branches. Preferably there are four branches.

Further in accordance with a preferred embodiment of the present invention the controller is pre-programmed or programmable to operate the valves in accordance with the operating cycle or in a high frequency mode.

Still further in accordance with a preferred embodiment of the present invention a pressure reducing valve is at the inlet of the manifold and is operative to reduce a pressure of the driving gas.

Additionally in accordance with a preferred embodiment of the present invention a regulating valve is fluidly connected to each of the ventilators for regulating flow of a driving gas through the ventilator.

In accordance with a preferred embodiment of the present invention the ventilator includes a housing with an air duct formed therethrough, a venturi tube mounted in the housing, and a second tube mounted in the housing with an opening into the air duct, the second tube being adapted for passage therethrough of a substance into the air duct. The substance may be an oxygen enrichment substance or a moisturizing additive.

Further in accordance with a preferred embodiment of the present invention the second tube is downstream of the venturi tube. Alternatively, the second tube is upstream of the venturi tube.

Still further in accordance with a preferred embodiment of the present invention the ventilator includes measurement apparatus mounted in the housing for measuring endotracheal pressure.

Additionally in accordance with a preferred embodiment of the present invention the ventilator includes a flow meter mounted in the housing for measuring flow of gas through the air duct.

In accordance with a preferred embodiment of the present invention the ventilator includes a transvector.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

Figure 1:
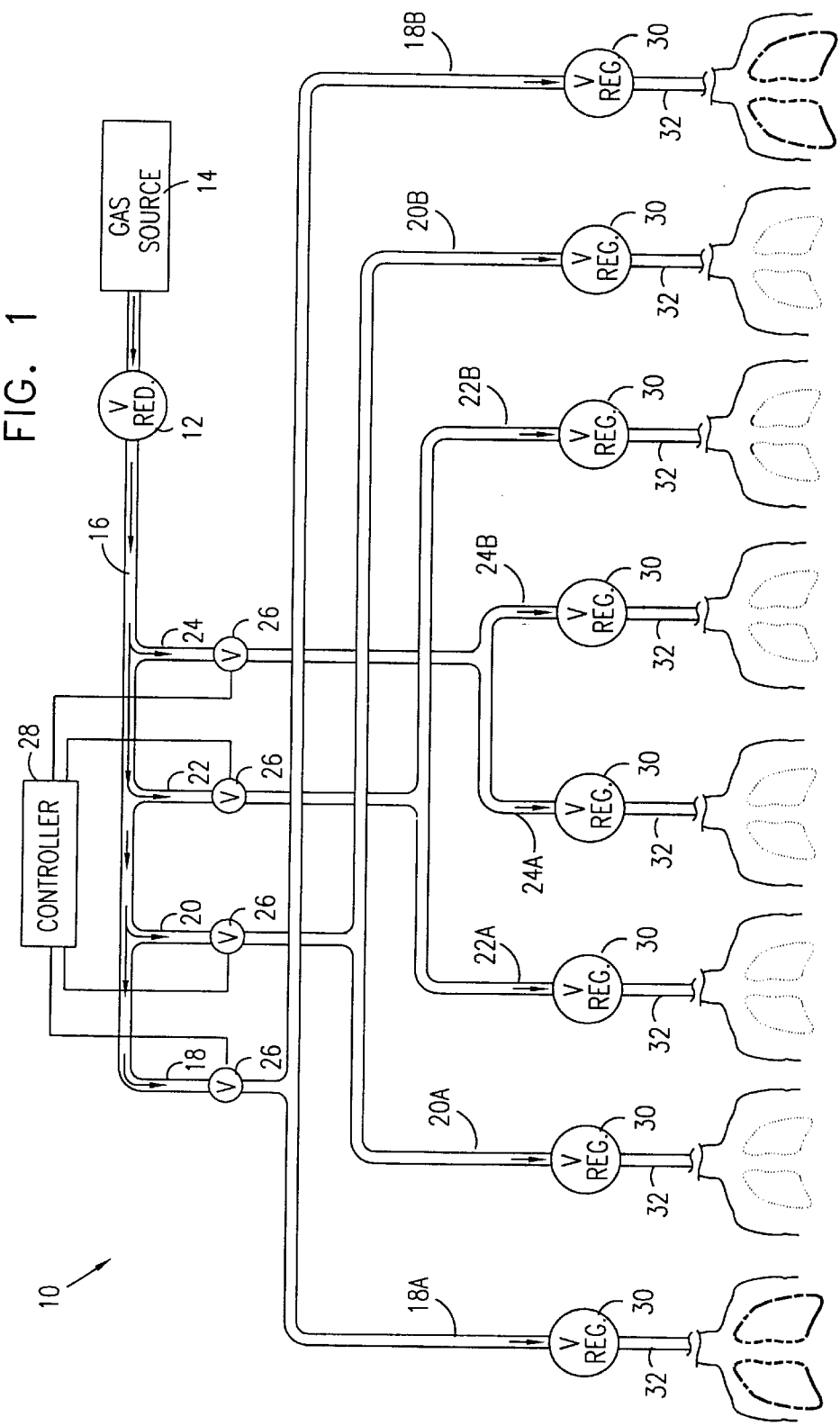
FIGS. 1–4 are simplified illustrations of a multiplex ventilation system constructed and operative in accordance with a preferred embodiment of the present invention, in four consecutive modes of operation, these modes making up one operating cycle.

Reference is now made to FIGS. 1–4 which illustrate a multiplex ventilation system 10 constructed and operative in accordance with a preferred embodiment of the present invention.

Ventilation system 10 preferably includes, at an inlet thereof, a pressure reducing valve 12 which receives a driving gas, such as air or oxygen, from a pressurized gas source 14, such as the familiar pressurized gas source built into hospital walls, or gas cylinder or compressor. Reducing valve 12 reduces the pressure of the driving gas to a suitable pressure, e.g., 35–45 PSI.

The gas flows from valve 12 to a manifold 16 fluidly connected thereto. Manifold 16 has a plurality of branches, four branches 18, 20, 22 and 24 being shown in the illustrated embodiment. It is noted that although four branches are considered to be the best mode of carrying out the invention, nevertheless other amounts of branches are possible within the scope of the invention.

Each branch includes a valve 26, preferably an electronically controlled valve, such as a solenoid, electrically connected, in wired or wireless manner, to a controller 28. Controller 28 may be pre-programmed to operate valves 26 in accordance with a predetermined operating cycle, or alternatively, may be programmable such that medical personnel can choose a desired operating cycle.

Each branch divides into two further sub-branches. In the illustrated embodiment, branches 18, 20, 22 and 24 respectively divide into sub-branches 18A, 18B, 20A, 20B, 22A, 22B, 24A and 24B. Each sub-branch includes a regulating valve 30 connected to a ventilator end-piece 32 (shown only schematically in FIGS. 1–4 for the sake of simplicity.) Ventilator end-piece 32 is preferably constructed basically as described in U.S. Pat. No. 4,495,946, and may be further provided with the improvements described hereinbelow with reference to FIGS. 5–7. Each ventilator end-piece 32 is connected to flexible endotracheal tube or breathing mask (not shown) for supplying the driving gas to lungs of a patient.

Operation of ventilation system 10 is based on the inhalation/exhalation ratio of the human breathing cycle. Inhalation is an active process wherein the diaphragm contracts and the lungs fill and become enlarged. Exhalation is a passive process wherein the diaphragm relaxes and the lungs elastically contract and expel gas therefrom. It is known that the active inhalation takes a shorter time than the passive exhalation, and in humans the inhalation/exhalation ratio is in the range of about 1:2 to 1:3.

In the best mode of carrying out the invention, ventilation system 10 causes inhalation of one branch while the other three branches are at rest, i.e., are in exhalation, and then sequentially causes inhalation of another branch, while the other three are maintained at rest. In this manner, for a given period of time, each of the four branches is in inhalation a quarter of the time and in exhalation three quarters of the time. For example, for a cycle of 6 seconds, the inhalation time is 1.5 sec and the exhalation time is 4.5 sec, which is a breathing cycle of 10 times per minute. As another example, for a cycle of 4 seconds, the inhalation time is 1 sec and the exhalation time is 3 sec, which is a breathing cycle of 15 times per minute. These two examples are quite satisfactory breathing cycles, since for a normal person, the rate is about 12 cycles per minute.

Since each branch 18, 20, 22 and 24 is subdivided into two sub-branches, it is possible to ventilate 8 patients simultaneously. This can be easily appreciated by examination of FIGS. 1–4. In FIG. 1, sub-branches 18A and 18B are supplied with the driving gas which causes expansion of the lungs of a pair of patients. Six other patients, connected to sub-branches 20A, 20B, 22A, 22B, 24A and 24B, are exhaling during the inhalation of the patients connected to sub-branches 18A and 18B.

Figure 2:
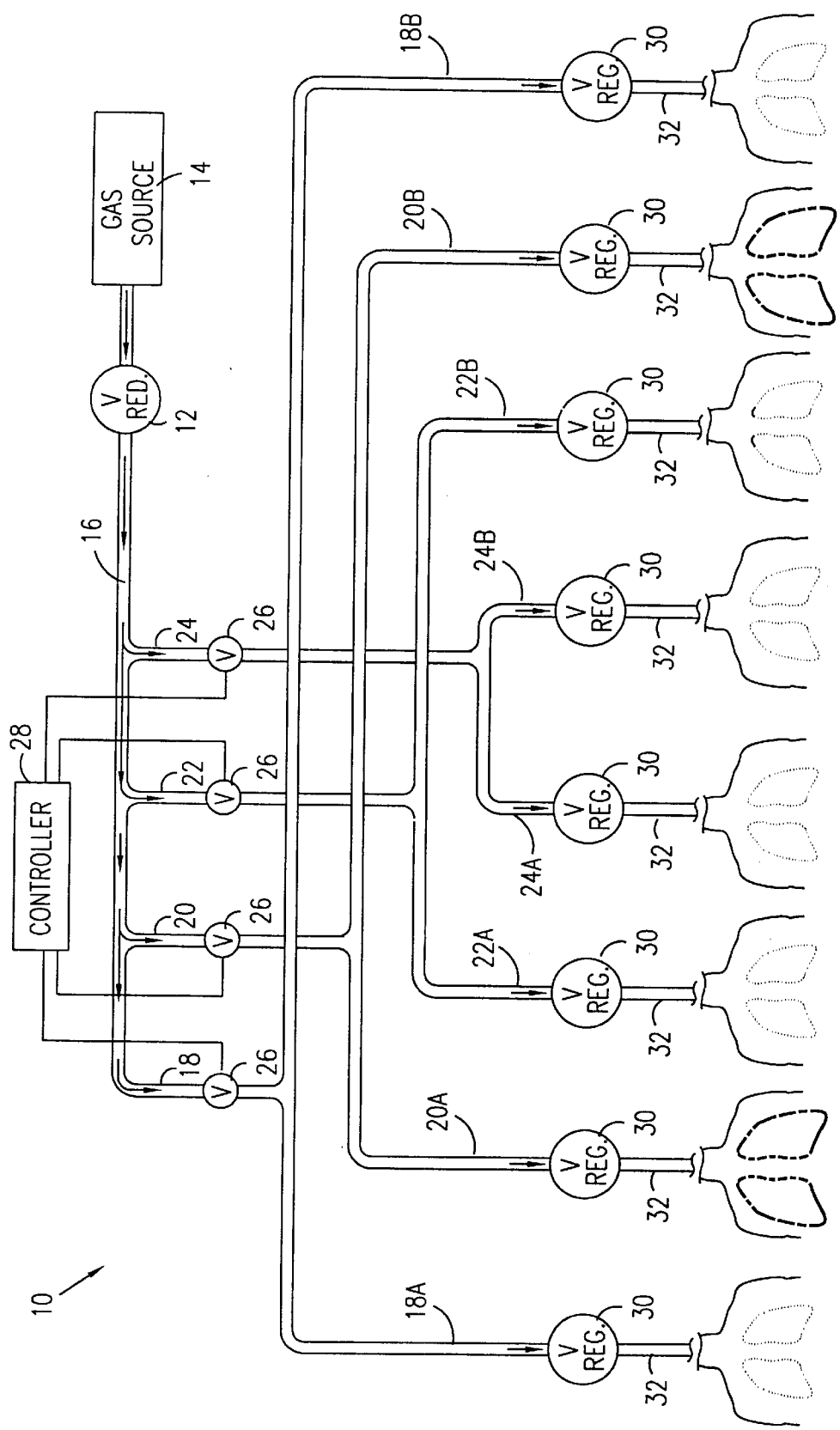

In FIG. 2, sub-branches 20A and 20B are supplied with the driving gas which causes expansion of the lungs of another pair of patients. The other six patients, connected to sub-branches 18A, 18B, 22A, 22B, 24A and 24B, are exhaling during the inhalation of the patients connected to sub-branches 20A and 20B.

Figure 3:
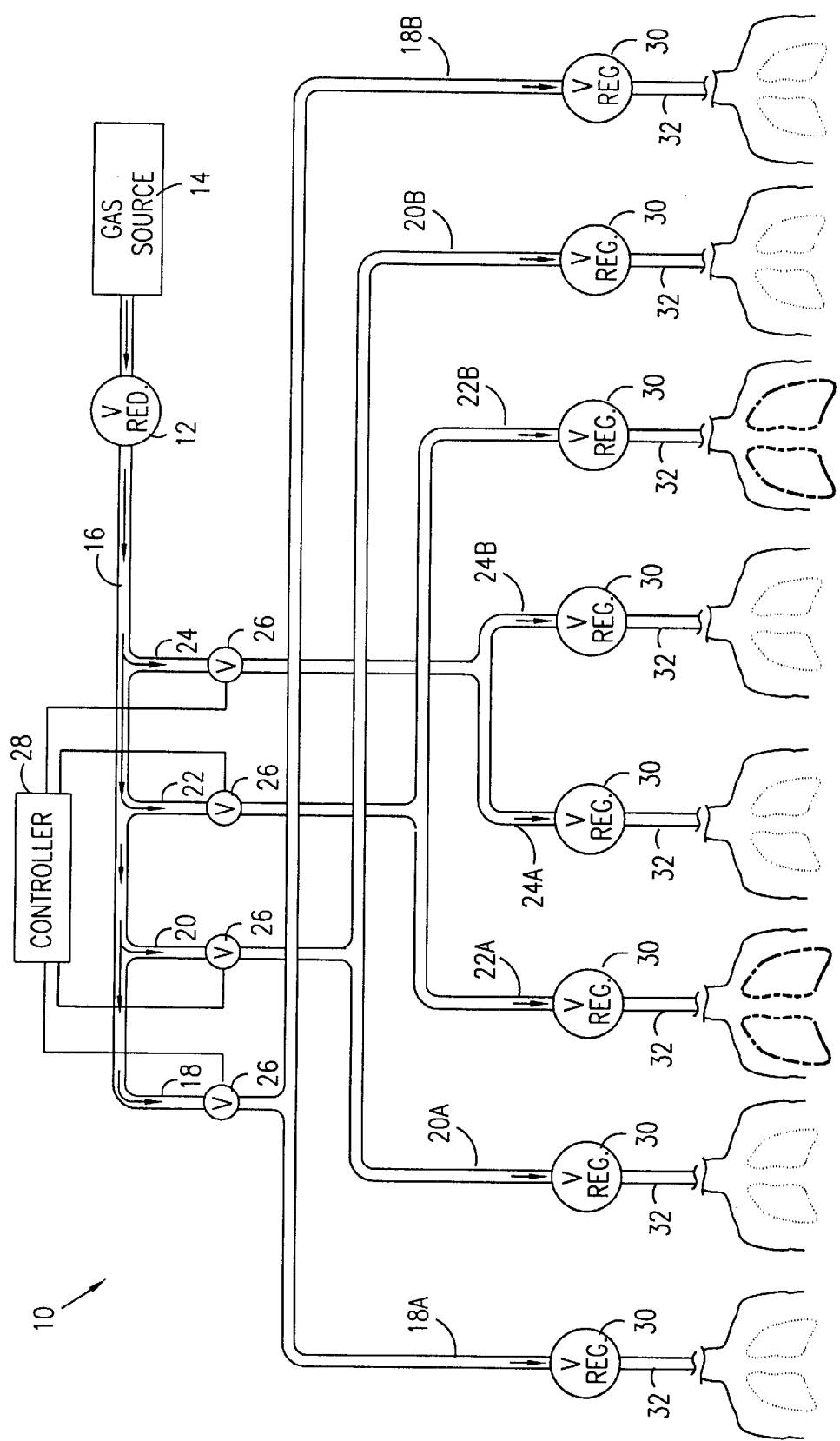

In FIG. 3, sub-branches 22A and 22B are supplied with the driving gas which causes expansion of the lungs of another pair of patients. The other six patients, connected to sub-branches 18A, 18B, 20A, 20B, 24A and 24B, are exhaling during the inhalation of the patients connected to sub-branches 22A and 22B.

Figure 4:
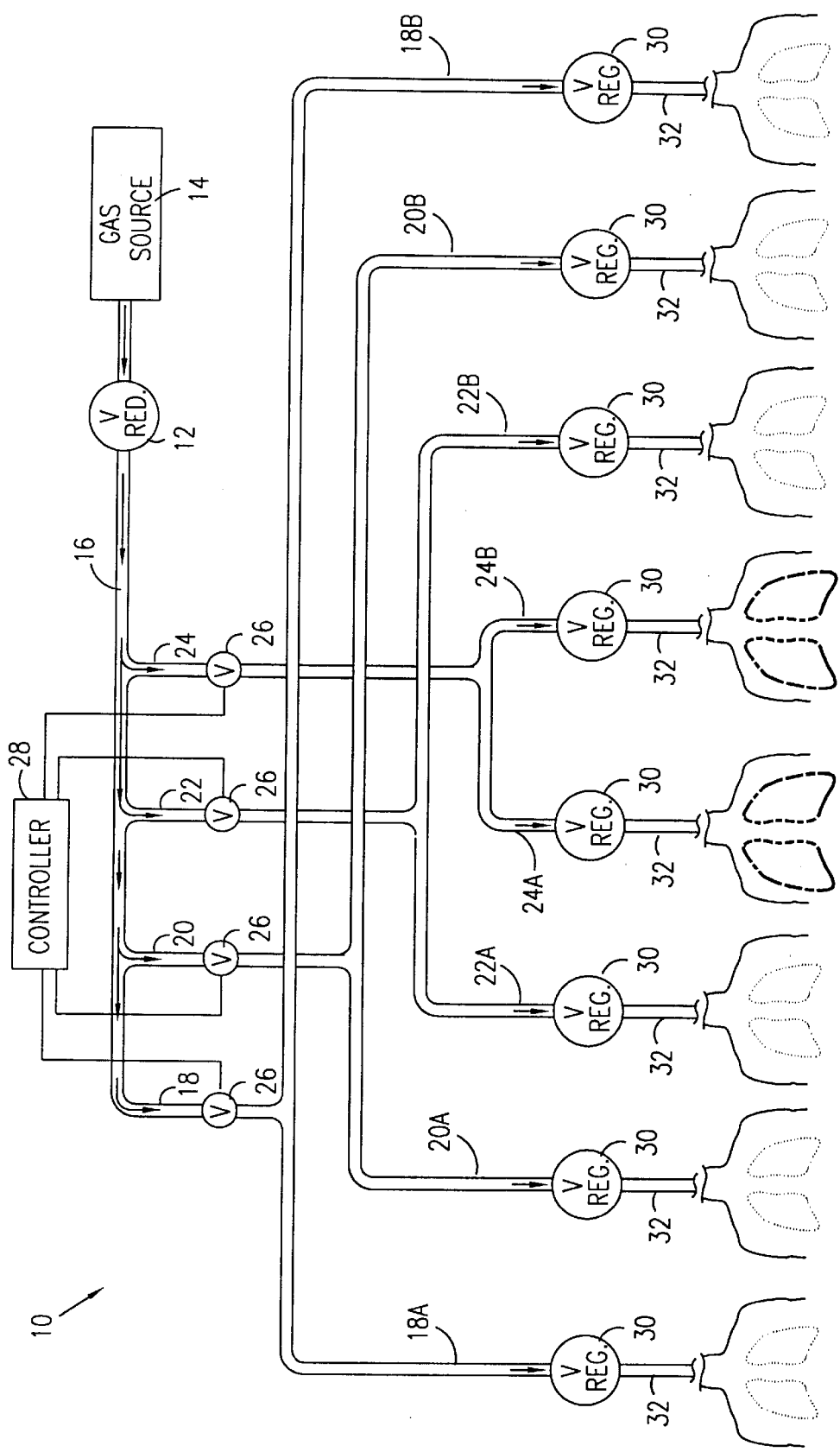

In FIG. 4, sub-branches 24A and 24B are supplied the driving gas which causes expansion of the lungs of another pair of patients. The other six patients, connected to sub-branches 18A, 18B, 20A, 20B, 22A and 22B, are exhaling during the inhalation of the patients connected to sub-branches 24A and 24B.

It is appreciated that any other number of branches and sub-branches is possible within the scope of the invention. For example, three branches may be employed wherein for each operating cycle,. ventilation system 10 causes inhalation of one branch while the other two branches are at rest, and then sequentially causes inhalation of another branch, while the other two are maintained at rest. In this manner, for a given period of time, each of the three branches is in inhalation a third of the time and exhalation two thirds of the time.

The volume of compressed gas which each patient receives during the inhalation period is determined by the setting of a regulating valve of ventilator end-piece 32, which is now described with reference to FIG. 5.

As mentioned above, ventilator end-piece 32 is preferably constructed basically as described in U.S. Pat. No. 4,495, 946. Briefly, the basic construction comprises a housing 40 which has a bore 42 formed therein in which is placed a valve stem of a regulating valve 44. Regulating valve 44 may be any kind of suitable valve, such as a pin valve, a gauge cock, a hole-against-hole type of valve, electronic valve and the like. An air duct 46 is preferably formed in a lower portion of housing 40, distanced from bore 42. Air duct 46 generally lies in a plane parallel to the plane of bore 42, the axes of bore 42 and air duct 46 being generally mutually perpendicular. Bore 42 communicates with air duct 46 via a connecting bore 48 generally centrally positioned in housing 40. A rigid venturi tube 50 is inserted in connecting bore 48 and leads into air duct 46. A flexible endotracheal tube 52 is preferably connected to a tubular connector 53 snugly attached to a distal end 54 of air duct 46. The proximal, open end 56 of air duct 46 may be connected to a three-way Rubin-type valve to which can be fitted a PEEP (positive end expiratory pressure) fitting or filter, not shown, as is known in the art. Oxygen enters venturi tube 50 and is injected via distal end 54 and endotracheal tube 52 to a patient's lungs.

Figure 5:
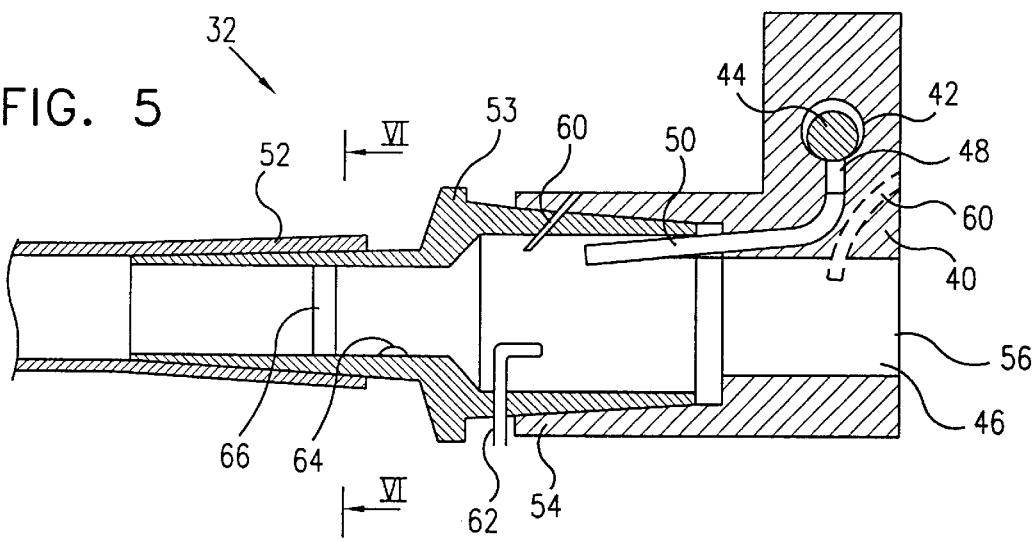
FIG. 5 is a simplified sectional illustration of a venturi-type ventilator constructed and operative in accordance with a preferred embodiment of the present invention.
Figure 6:
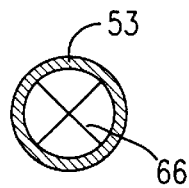
FIG. 6 is a simplified sectional illustration of a flow meter useful with the ventilator of FIG. 5, taken along lines VI—VI in FIG. 5.

In accordance with a preferred embodiment of the present invention a small tube 60 is mounted in housing 40 with an opening into air duct 46, most preferably downstream of venturi tube 50, but alternatively may be upstream thereof as shown in broken lines in FIG. 5. Tube 60 may be employed to introduce therethrough various substances to enhance performance of tentilator end-piece 32, such as oxygel-enrichment substances or moisturizing additives for humidification purposes, for example.

Additionally or alternatively, a tube 62 may be placed in some portion of the distal end 54 (or tubular connector 53) for endotracheal pressure measurement. Alternatively, instead of tube 62, a pressure transducer or sensor 64 may be mounted in some portion of the distal end 54 for endotracheal pressure measurement.

Additionally or alternatively, a flow meter 66 may be placed in some portion of the distal end 54 (or tubular connector 53) for measuring flow of gas to the patient. Flow meter 66 is shown as a hot-wire anemometer (see also FIG. 6), but it is well appreciated by persons skilled in the art that many other types of flow meters may be used as well.

Figure 7:
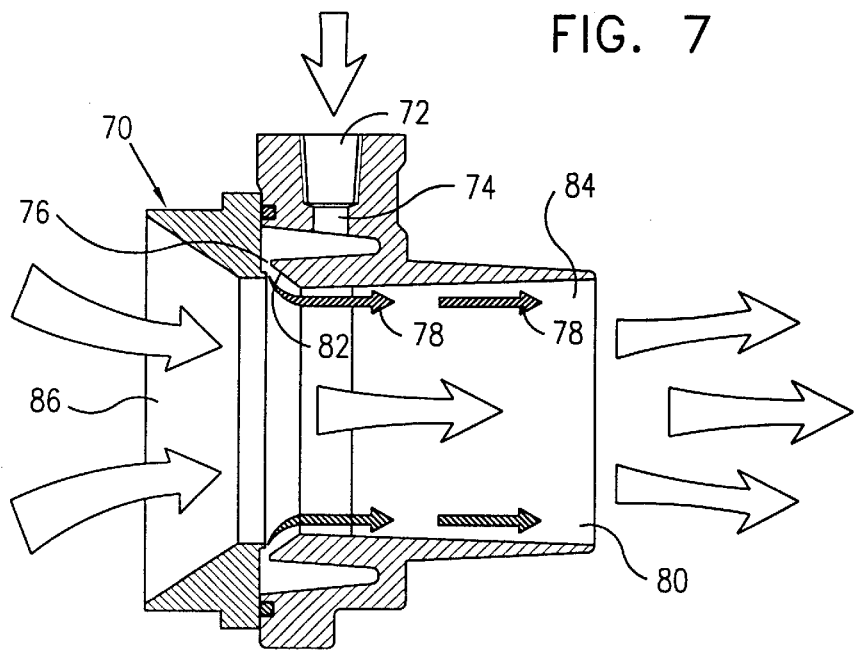
FIG. 7 is a simplified sectional illustration of a transvector-type ventilator constructed and operative in accordance with a preferred embodiment of the present invention.

Reference is now made to FIG. 7 which illustrates an alternative construction of the ventilator, in accordance with another preferred embodiment of the present invention. In this embodiment, the ventilator includes a transvector 70. Transvectors are commercially available from Vortec Corporation, Cincinnati, Ohio, USA. Transvectors work on the Coanda principle that a flowing fluid will attach itself to an adjacent wall and can change direction in accordance with wall contours. Use of transvectors in bronchoscopy is discussed in J. Lemer et al., "Fiberoptic Bronchoscopy with General Anesthesia using a Transvector for Ventilation", Chest, 90:4, 613–614 (Oct. 1986), the disclosure of which is incorporated herein by reference.

Referring to FIG. 7, transvector 70 has an inlet 72 through which flows the driving gas, e.g., oxygen, into a plenum chamber 74 surrounding and communicating with a ring-shaped nozzle 76. Ring-shaped nozzle 76 is typically only about 0.05 mm wide and throttles the oxygen to atmospheric pressure, the oxygen attaining sonic velocity as a result of the throttling. The thin sheet of high velocity oxygen, designated by arrows 78, is deflected toward an outlet 80 by a small lip 82 and moves along the interior surfaces of transvector 70 and through its throat 84. The small particles of high-velocity oxygen collide with still or relatively slow particles of gas (e.g., air) in an inlet region 86 of transvector 70. This causes the slow or still particles to accelerate and the fast particles to decelerate. In this manner, the flow of oxygen sacrifices velocity to induce larger amounts of air into the stream and an amplified flow moves through throat 84. Transvector 70 can amplify fluid flows by a factor of 20 as opposed to 8 achievable with a venturi injector of the type shown in FIG. 5.

Transvector 70 can also be connected to a three-way Rubin-type valve, to which can be fitted a PEEP (positive end expiratory pressure) fitting or filter (not shown) at its inlet region, and at its outset region can be connected to an endotracheal tube or breathing mask, as is known in the art.

Figure 8:
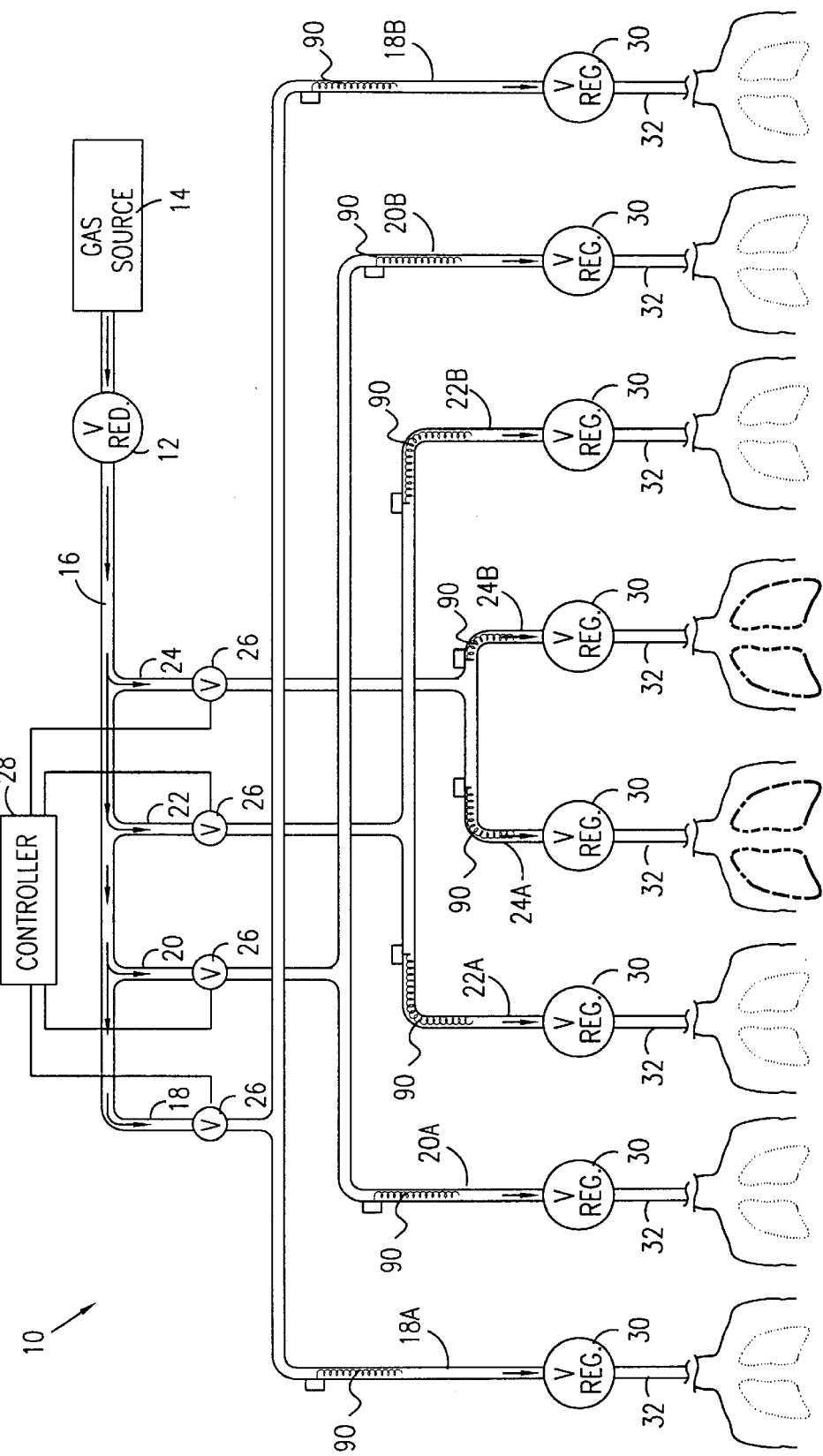
FIG. 8 is a simplified illustration of a multiplex ventilation system constructed and operative in accordance with another preferred embodiment of the present invention.

Reference is now made to FIG. 8 which illustrates another variation of multiplex ventilation system 10 constructed and operative in accordance with another preferred embodiment of the present invention. In this embodiment, one or more heating elements 90 are placed on one or more of the branches 18, 20, 22 and 24. Most preferably heating elements 90 are electrical heating elements that extend over the last 50–100 cm of the sub-branches 18A, 18B, 20A, 2B, 22A, 22B, 24A and 24B prior to the connection to regulating valves 30. This enables the inspired air to be heated to body temperature before entering ventilator end-pieces 32.

It will be appreciated by persons skilled in the art that the present invention is not limited by what has been particularly shown and described hereinabove. Rather the scope of the present invention includes both combinations and sub-combinations of the features described hereinabove as well as modifications and variations thereof which would occur to a person of skill in the art upon reading the foregoing description and which are not in the prior art.

What is claimed is:

1. A ventilation system comprising:
   a manifold fluidly connectable at an inlet thereof to a pressurized source of a driving gas, said manifold having a plurality of branches;
   an electronically controlled valve fluidly connected to each said branch downstream of the inlet of said manifold;
   a ventilator end-piece fluidly connected to each of said branches downstream of said valves, each said ventilator end-piece being operative to force a driving gas into lungs of a patient; and
   a controller in electrical communication with said valves, said controller operating said valves in accordance with an operating cycle comprising:
   a) causing a driving gas to flow through one of said ventilator end-pieces while substantially preventing flow of the driving gas through the other ventilator end-pieces;
   b) causing the driving gas to flow to another one of said ventilator end-pieces which previously had no driving gas flowing therethrough, while substantially preventing flow of the driving gas through the other ventilator end-pieces including the ventilator end-piece which previously had the driving gas flowing therethrough; and
   c) sequentially repeating steps a) and b) until all the ventilator end-pieces have had the driving gas flow therethrough.

2. The ventilation system according to claim 1 wherein each said branch divides into two sub-branches.

3. The ventilation system according to claim 1 comprising four said branches.

4. The ventilation system according to claim 1 wherein said controller is pre-programmed to operate said valves in accordance with the operating cycle.

5. The ventilation system according to claim 1 wherein said controller is programmable to operate said valves in accordance with the operating cycle.

6. The ventilation system according to claim 1 and further comprising a pressurized source of a driving gas fluidly connected to the inlet of said manifold.

7. The ventilation system according to claim 6 and further comprising a pressure reducing valve at the inlet of said manifold which is operative to reduce a pressure of the driving gas.

8. The ventilation system according to claim 1 and further comprising a regulating valve fluidly connected to each of said ventilator end-pieces for regulating flow of a driving gas through said ventilator end-piece.

9. The ventilation system according to claim 1 wherein said ventilator end-piece comprises:

a housing with an air duct formed therethrough, a venturi tube mounted in said housing, and a second tube mounted in said housing with an opening into said air duct, said second tube being adapted for passage therethrough of a substance into said air duct.

10. The ventilation system according to claim 9 wherein said substance comprises at least one of an oxygen enrichment substance and a moisturizing additive.

11. The ventilation system according to claim 9 wherein said second tube is downstream of said venturi tube.

12. The ventilation system according to claim 9 wherein said second tube is upstream of said venturi tube.

13. The ventilation system according to claim 1 wherein said ventilator end-piece comprises:

a housing with an air duct formed therethrough, a venturi tube mounted in said housing, and measurement apparatus mounted in said housing for measuring endotracheal pressure.

14. The ventilation system according to claim 1 wherein said ventilator end-piece comprises:

a housing with an air duct formed therethrough, a venturi tube mounted in said housing, and a flow meter mounted in said housing for measuring flow of gas through said air duct.

15. The ventilation system according to claim 1 wherein said ventilator end-piece comprises a transvector.

16. The ventilation system according to claim 1 and further comprising at least one heating element operative to heat said driving gas prior to entrance into said ventilator end-pieces.

* * * * *